US011033235B2

(12) United States Patent
Tambe et al.

(10) Patent No.: US 11,033,235 B2
(45) Date of Patent: Jun. 15, 2021

(54) METHOD AND APPARATUS FOR MOTION ARTIFACT REDUCTION IN ECG HARNESS

(71) Applicant: NimbleHeart Inc., Sunnyvale, CA (US)

(72) Inventors: Sonal Tambe, Saratoga, CA (US); Pramod Deshmukh, Sayre, PA (US); Swanand Sardesai, Irvine, CA (US)

(73) Assignee: NimbleHeart Inc., Sunnyvale, CA (US)

( * ) Notice: Subject to any disclaimer, the term of this patent is extended or adjusted under 35 U.S.C. 154(b) by 0 days.

(21) Appl. No.: 14/037,695

(22) Filed: Sep. 26, 2013

(65) Prior Publication Data

US 2014/0378848 A1 Dec. 25, 2014

Related U.S. Application Data (60) Provisional application No. 61/837,059, filed on Jun. 19, 2013.

(51) Int. Cl.
| | |
|---|---|
| *A61B 5/04* | (2006.01) |
| *A61B 5/00* | (2006.01) |
| *A61B 5/0205* | (2006.01) |
| *A61B 5/11* | (2006.01) |
| *A61B 5/024* | (2006.01) |
| *A61B 5/0245* | (2006.01) |

(Continued)

(52) U.S. Cl.
CPC ............ *A61B 5/721* (2013.01); *A61B 5/0205* (2013.01); *A61B 5/0245* (2013.01); *A61B 5/02438* (2013.01); *A61B 5/11* (2013.01); *A61B 5/259* (2021.01); *A61B 5/282* (2021.01); *A61B 5/6831* (2013.01)

(58) Field of Classification Search
CPC ... A61B 5/721; A61B 5/04087; A61B 5/6831; A61B 5/6833; A61B 5/6832; A61B 5/6804; A61N 1/0484; A61L 15/58

USPC ................. 600/372, 386–391, 393, 508–509
See application file for complete search history.

(56) References Cited

U.S. PATENT DOCUMENTS 4,608,987 A * 9/1986 Mills ............................. 600/389
5,445,149 A * 8/1995 Rotolo ............... A61B 5/04085
600/382

(Continued)

OTHER PUBLICATIONS

Ding, Jim. "Gentle Silicone Gel Adhesive Systems Revolutionize Direct Skin Pressure Sensitive Adhesives". Jul. 2008. https://news.thomasnet.com/companystory/gentle-silicone-gel-adhesive-systems-revolutionize-direct-skin-pressure-sensitive-adhesives-547319.*

*Primary Examiner* — Joseph A Stoklosa
*Assistant Examiner* — Brian M Antiskay
(74) *Attorney, Agent, or Firm* — Mahesh Law Group PC; Kumar Maheshwari (57) ABSTRACT

A motion artifact reduction apparatus and method of using a motion artifact reduction apparatus are provided. A general aspect of a motion artifact reduction apparatus includes at least one of a plurality of sensors and at least one sleeve body with a first end and a second end. The motion artifact reduction apparatus further includes a means for removably attaching the first end and the second end to each other and at least one sensor port disposed within the at least one sleeve body. The motion artifact reduction apparatus further includes an adhesive layer disposed around the sensor port, wherein the motion artifact of the at least one of a plurality of sensors may be reduced by attaching the first end and the second end of the sleeve body to each other and by the contact of the adhesive layer to the user's body at a desirable location.

9 Claims, 7 Drawing Sheets

(51) Int. Cl.
    *A61B 5/259*    (2021.01)
    *A61B 5/282*    (2021.01)

(56) References Cited

U.S. PATENT DOCUMENTS

| | | | |
|---|---|---|---|
| 7,822,471 B2 | 10/2010 | Bowers | |
| 8,301,218 B2 * | 10/2012 | Nguyen | A61B 5/0478 |
| | | | 600/372 |
| 8,428,682 B1 * | 4/2013 | Rood | A61B 5/0408 |
| | | | 600/391 |
| 8,798,710 B2 | 8/2014 | Chi | |
| 8,914,099 B2 | 12/2014 | Yazicioglu et al. | |
| 9,192,313 B1 * | 11/2015 | Lisy | A61B 5/0408 |
| 9,642,575 B2 | 5/2017 | Freeman et al. | |
| 9,872,652 B2 | 1/2018 | Salehizadeh et al. | |
| 9,931,081 B2 | 4/2018 | Wang et al. | |
| 2004/0260167 A1 * | 12/2004 | Leonhardt | A61B 5/0536 |
| | | | 600/390 |
| 2005/0261564 A1 * | 11/2005 | Ryu | A61B 5/282 |
| | | | 600/388 |
| 2005/0277821 A1 * | 12/2005 | Payne, Jr. | A61B 5/04 |
| | | | 600/383 |
| 2006/0084855 A1 * | 4/2006 | Teschner et al. | 600/390 |
| 2008/0114232 A1 * | 5/2008 | Gazit | A61B 5/04085 |
| | | | 600/390 |
| 2008/0287770 A1 * | 11/2008 | Kurzweil | A61B 5/0408 |
| | | | 600/388 |
| 2012/0035435 A1 * | 2/2012 | Choi | A61B 5/6831 |
| | | | 600/301 |
| 2012/0310070 A1 * | 12/2012 | Kumar et al. | 600/391 |

* cited by examiner

METHOD AND APPARATUS FOR MOTION ARTIFACT REDUCTION IN ECG HARNESS

BACKGROUND

An ECG sensor harness is a desirable form of a device that can be used by the people for home based cardiac monitoring and that does not require any hook up by medical professionals. The device needs to detect anomalies including, but not limited to, myocardial infarctions (MI), ischemia and arrhythmia. The ECG harnesses that are currently available provide limited information and limited performance. One of the causes for the performance limitation of these systems may be motion artifacts.

Motion artifacts may occur when the subject is in motion during exercise or even moderate movement. Motion artifacts in the ECG signal may be realized in an impedance change seen by the sensor. A distorted signal can result in improper detection of ST segment changes in ECG. In many current solutions to detect ST segment changes, the user must remain relatively still to reduce or eliminate motion artifacts that may interfere with the performance of the system. This makes the detection of exercise-induced Ischemia difficult, if not impossible. The motion artifacts may be divided into two distinct components, those normal to the sensor-body interface and shear those tangential to the sensor-body interface. It is desirable to have a solution that either eliminates or minimizes both of these components so that clinical quality ST changes detection is possible with the obtained ECG signal.

Some solutions attempt to reduce motion artifacts using additional normal force to push the sensors on the body. However they are not sufficient in mitigating the motion artifacts. Harnesses are designed based on dry electrodes typically and the dry electrodes can't control shear movement of the sensors.

In this respect, before explaining at least one embodiment of the invention in detail, it is to be understood that the invention is not limited in its application to the details of construction and to the arrangement of the components set forth in the following description or illustrated in the drawings. The invention is capable of other embodiments and of being practiced and carried out in various ways. In addition, it is to be understood that the phraseology and terminology employed herein are for the purpose of description and should not be regarded as limiting.

SUMMARY OF THE INVENTION

The present invention may be comprised of at least one of a plurality of motion artifact reduction components in or on the harness. These components may be comprised of, but not limited to, springs, liquid or semi-liquid or semi-solid adhesive, adhesive pads, adhesive tape, snaps, hook and pile closures, other attachment means of similar physical or fastening characteristics.

In one or more embodiments, the components may be used to reduce the motion artifacts of one or more of a plurality of ECG electrodes.

In one or more embodiments, the components may also be made of hyper-elastic material that stretches and compresses an electrode spring producing normal force on sensor.

In one embodiment, the electrodes used for this may be dry contact solid metal sensors. The metal may be advantageously chosen for its physical characteristics and may be plated for optimal sensitivity. The electrode may be shaped to fit particular electrical or positional characteristics.

In one embodiment, the electrodes may be made of brass or stainless steel for strength and gold-plated to increase conductivity.

In one embodiment, the electrode may be round, ovoid, or rectangular in shape.

In one or more embodiments, the sensors may be a two-part sensor; the two-part sensor may be further comprised of a permanent sensing element and a removable, separately fastened or self-adhesive element.

In one or more embodiments, the self-adhesive element may be made of material such as silicone, gel, or neoprene.

In one or more embodiment, the sensing element may further comprise a spring backing on each sensor that can push the sensor towards the human body giving normal force during motion to keep the sensor in constant with the human body. The spring can be made of any material, including but not limited to, metal, plastic or rubber or other resilient or semi-resilient material or combination of materials. The spring can be any shape: conventional helical, beam which produces spring force by deflection.

In one or more embodiments, motion artifact mitigation design is used to resolve the movement of an electrode away from a desired location on a human body.

In one or more embodiments, the self-adhesive element may further comprise a sleeve-type construction. The sensor may be placed within the sleeve. The sleeves may adhere to the human body. The sleeves may produce increased shear resistance and mitigate the shear movement of the sensor relative to the body.

In one or more embodiments, the sleeve may be implemented either as a removable assembly mounted on the harness.

In one or more embodiments, the sleeve maybe permanently attached to the harness by processes including, but not limited to, stitching, gluing, or molding.

In one or more embodiments, the sleeve may be integrated into the construction of the harness.

One or more embodiments of the invention may be use for symptomatic cardiac monitoring or for cardiac monitoring during a physical activity for telemedicine or for continuous monitoring away from a hospital.

In one or more embodiments, this invention may also be used as a reliable, compact and first level of screening device in emergency situations, as a replacement for traditional twelve lead ECG machine in remote scenarios including those in flights or extraterrestrial environments on in Emergency rooms to give immediate real time indication of the risk of cardiac events to the patient.

Cardiac rehab patients as well as other at-risk patients can use the invention. Home cardiac rehab patients may also benefit from the invention. Individuals concerned about fitness can benefit from this invention by regulating their exercise to remain within safe cardiac stress levels. The invention may further be implemented as a reusable Holter monitor.

In another embodiment, this invention may be used to monitor chronic or recurring body functions or conditions, such as snoring or sleep apnea, and report the conditions back to a doctor, researcher, or other health care professional.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention. Therefore, the foregoing is considered as illustrative only of the principles of the invention.

Further, since numerous modifications and changes will readily occur to those skilled in the art, it is not desired to limit the invention to the exact construction and operation shown and described, and accordingly, all suitable modifications and equivalents may be resorted to, falling within the scope of the invention.

Other objectives, features and advantages of the invention will become apparent from the following description and drawings wherein.

DETAILED DESCRIPTION

Figure 1:
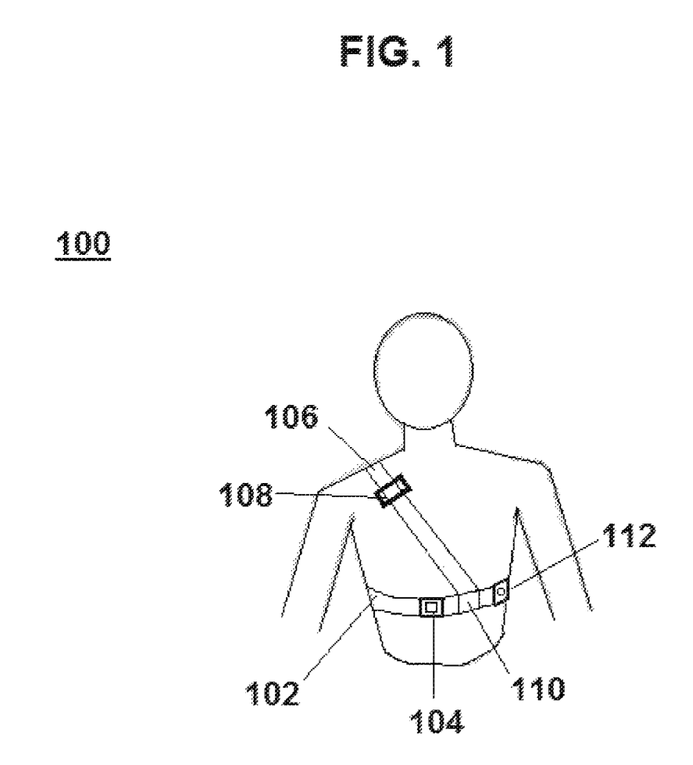
FIG. 1 is a front view of the preferred embodiment.

Referring now to FIG. 1, in one embodiment, the monitor and harness assembly 100 may be comprised of at least a first of a plurality of retaining means 102 across the body. The first of the at least one of a plurality of retaining means 102 may further comprise an adjustment means 104 to adjust the size of the first of at least one of a plurality of retaining means 102. The adjustment means 104 may comprise one or more of a buckle, a snap, a hook and pile closure, a tension adjustment or a means of adjustment of similar physical use or characteristics.

The retaining means may further comprise at least two retaining means, a first retaining means 102 and a second retaining means 106. The second retaining means 106 may further comprise a second adjustment means 108. The adjustment means 108 may comprise one or more of a buckle, a snap, a hook and pile closure, a tension adjustment or a means of adjustment of similar physical use or characteristics.

The second retaining means 106 may have a first and a second end. The first end may be fixedly or removably attached to the first retaining means 102. The second retaining means 106 may then be positioned across the chest of the wearer and the second end of the first retaining means 102 be fixedly or removably attached to the first retaining means 102.

In or more embodiments, the second retaining means 106 may further comprise one or more retaining means across at least one of the user's shoulders to position the first retaining means 102 on the body of the user accordingly.

In one or more embodiments, the first and second ends of the second retaining means 106 may be fixedly or removably attached to the first retaining means 102 the first end towards the front of the user 110 and the second end towards the rear of the user (not pictured).

In one or more embodiments, at least a first electrode 112 is positioned at an appropriate position to acquire a signal from the user's body.

Figure 2:
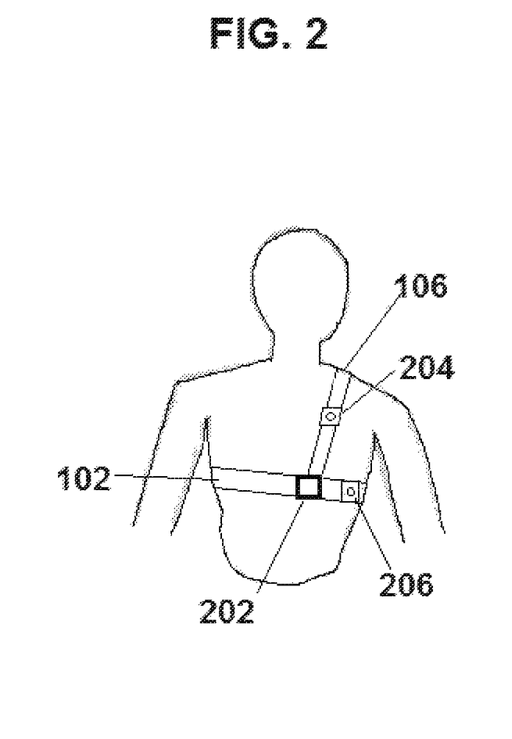
FIG. 2 is a rear view of the preferred embodiment.

Referring now to FIG. 2, in one or more embodiments, the rear view of the monitor and harness assembly may be a mirror image of the front view. Here, the first retaining means 102 still encircles the user. Additionally, in one or more embodiments, the second retaining means 106 may be fixedly or removably attached to the first retaining means 102 the second end towards the rear of the user.

In one or more embodiment, ECG acquisition unit 202 may be positioned on the first retaining means 102.

Electrodes 204 and 206 may be placed at strategic positions on the body to acquire the vector across the human heart so as to capture maximum number of ischemic and infarction events.

Figure 3:
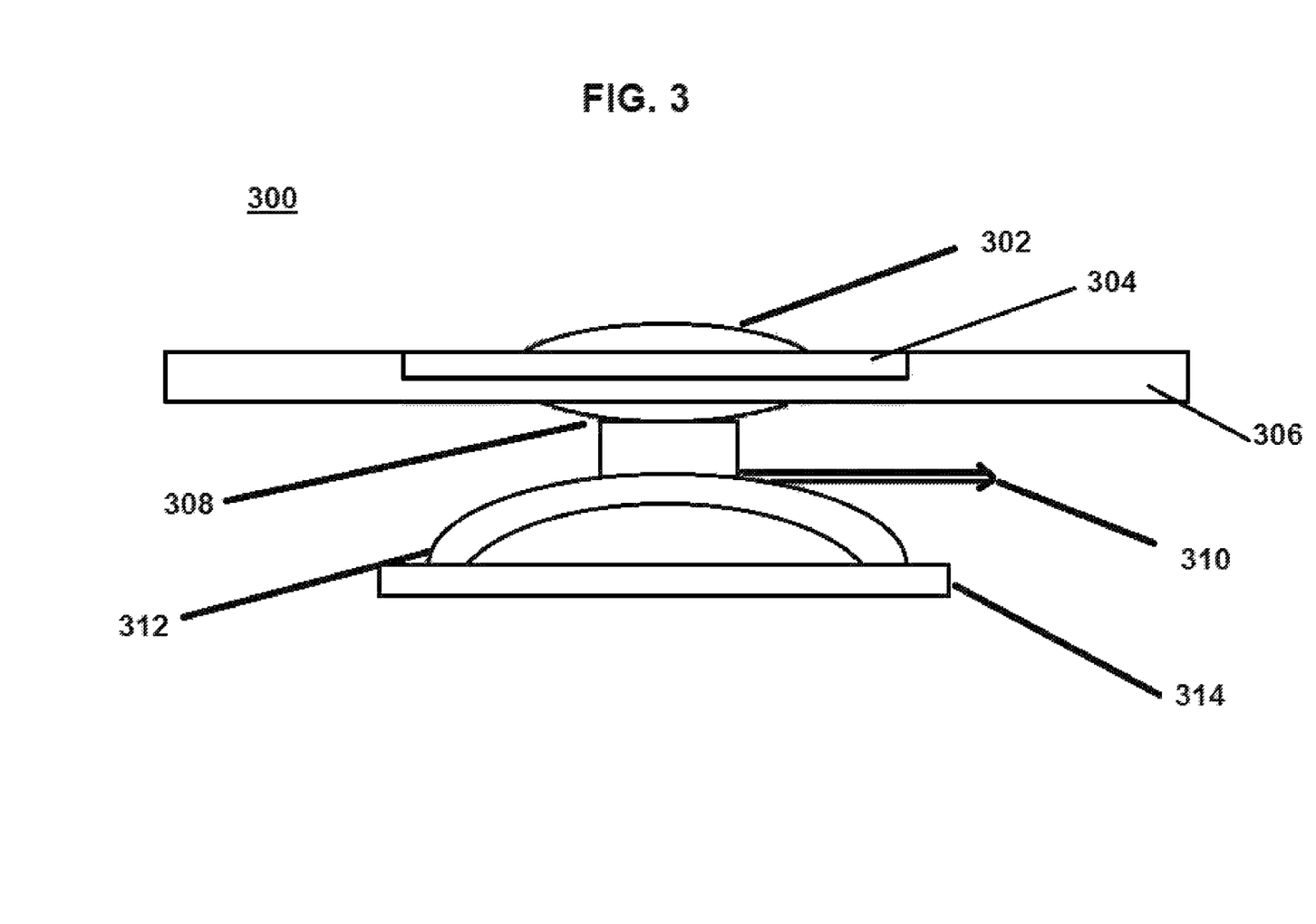
FIG. 3 is a side view of the preferred embodiment of an electrode.

Referring now to FIG. 3, the ECG electrode assembly 300 is comprised of a gold plated stainless steel sensor 302 surrounded by an adhesive layer 304.

The retaining means 102 and 106 (not pictured) may be composed of an outward-facing ("outer") layer 306 and an inward-facing ("inner") layer 314.

The adhesive layer 304 is disposed around the gold-plated stainless steel sensor 302 and within a portion of the outer layer of retaining means 306. The outer layer of retaining means 306 is disposed between the adhesive layer 304 and the backside of the electrode 308.

In one or more embodiments, the ECG electrode assembly 300 may include an electrode cable connection 310. The electrode cable connection 310 is electrically connected to the harness spring 312. The harness spring 312 is disposed between the backside of the electrode 308 and the inner layer of the retaining means 314 and provides normal force to ensure a good point of contact.

Figure 4:
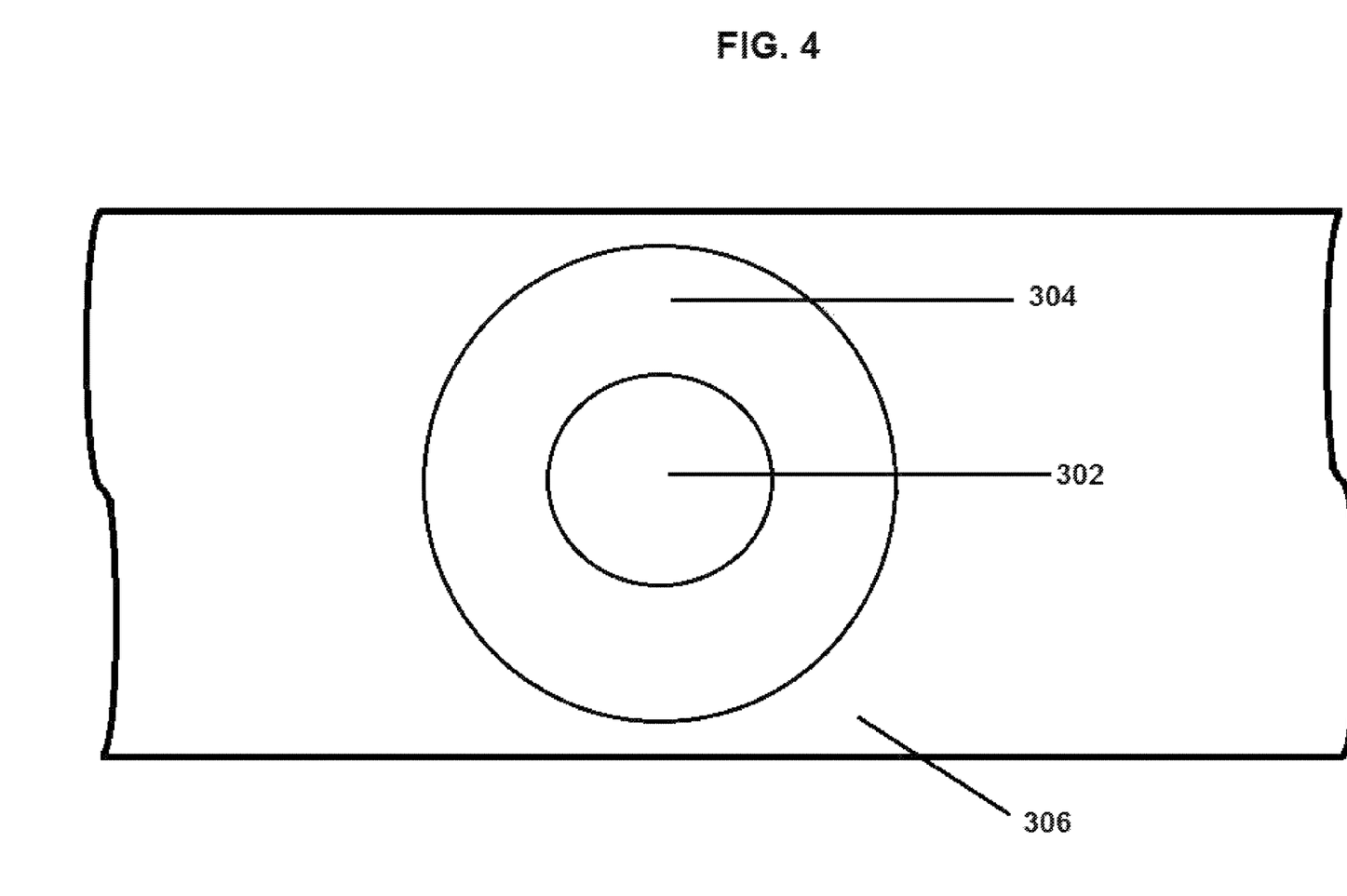
FIG. 4 is a top view of the preferred embodiment of an electrode.

Referring now to FIG. 4, the adhesive layer 304 is disposed around the sensor 302 and within a portion of the outer layer of retaining means 306.

Figure 5:
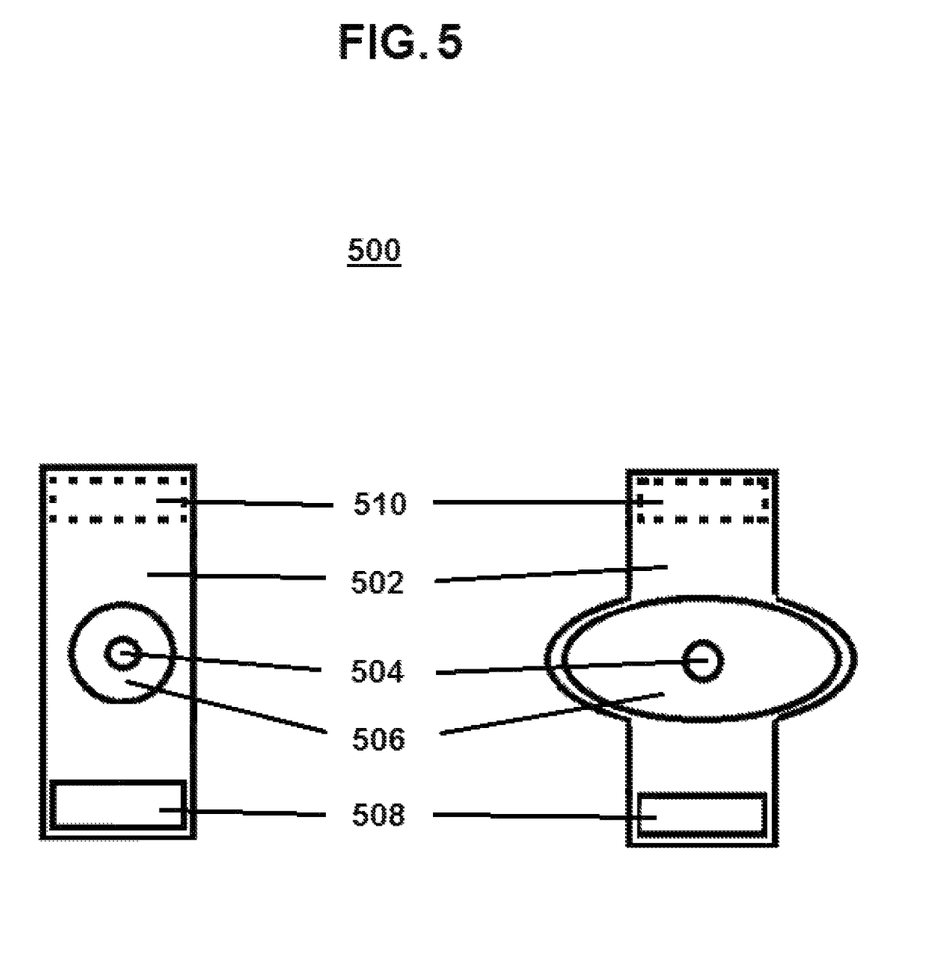
FIG. 5 is a top view of exemplary embodiments of a sleeve.

Referring now to FIG. 5, sleeve assembly 500, shown in two different embodiments, is comprised of a sleeve body 502. Sleeve body 502 may, within its length and width, further define and comprise a sensor port 504. Sensor port 504 may be of any convenient shape through with a sensor may extend to contact, or close to within the required distance of, the user's skin or other necessary body part. Disposed around sensor port 504 and upon sleeve body 502, is a movement reduction adhesive layer 304. Adhesive layer 304 may be comprised of an adhesive or semi-adhesive material, such as a silicone gel. Sleeve fastening means 508 and 510 may be disposed on opposite sides of the sleeve body 502, wherein the sleeve may be removably attached at advantageous positions on the harness to further reduce the motion of the sensor upon the user's body by avoiding shear movement.

Figure 6:
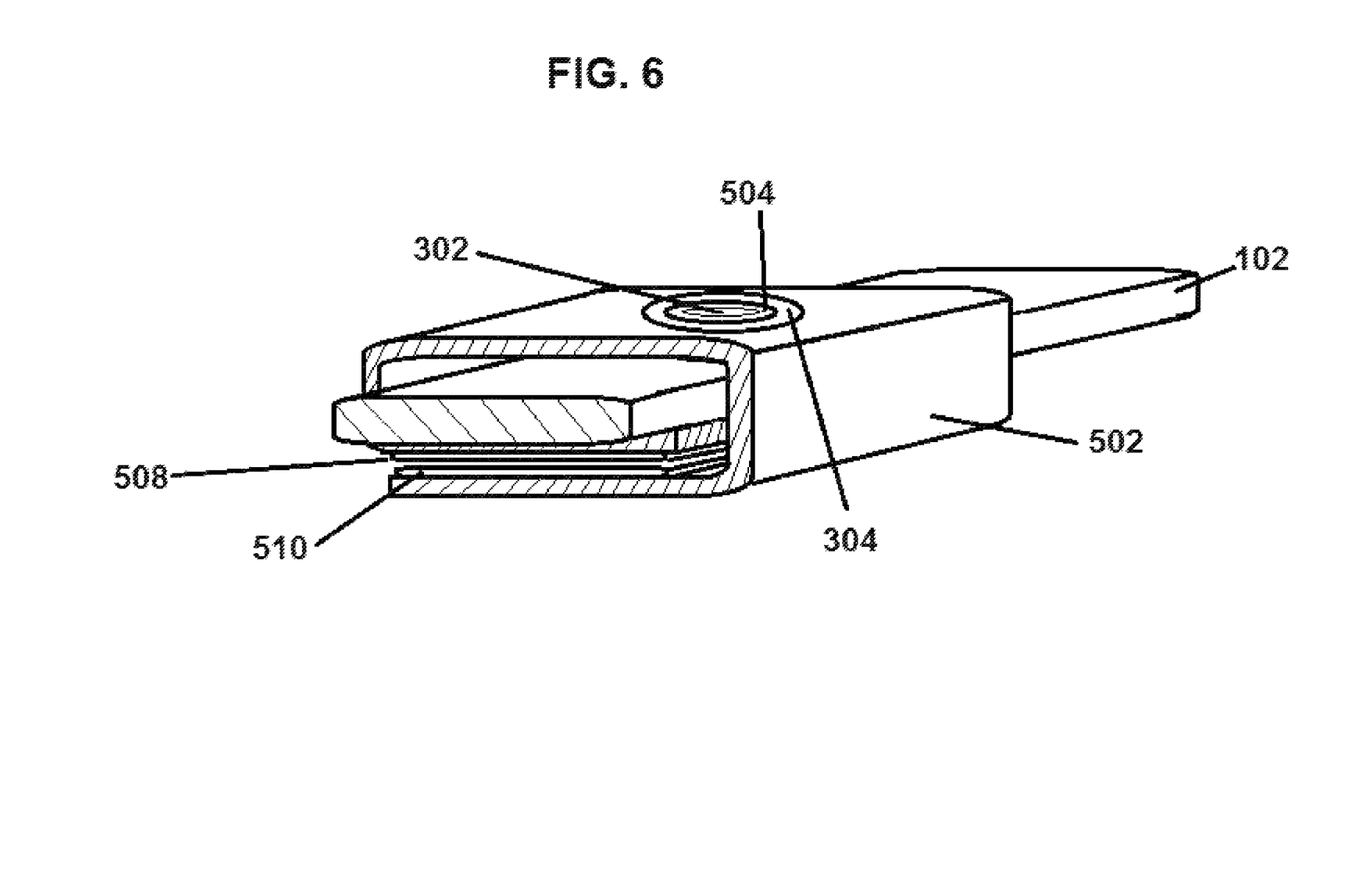
FIG. 6 is a perspective view of an exemplary embodiment of a sleeve.

Referring now to FIG. 6, which depicts the sleeve body 502 wrapped around the first retaining means 102 and attached by sleeve fastening means 508 and 510. This configuration removably affixes the electrode 302, which is protruding through the sensor port 504, and is surrounded by the adhesive layer 304.

Figure 7A:
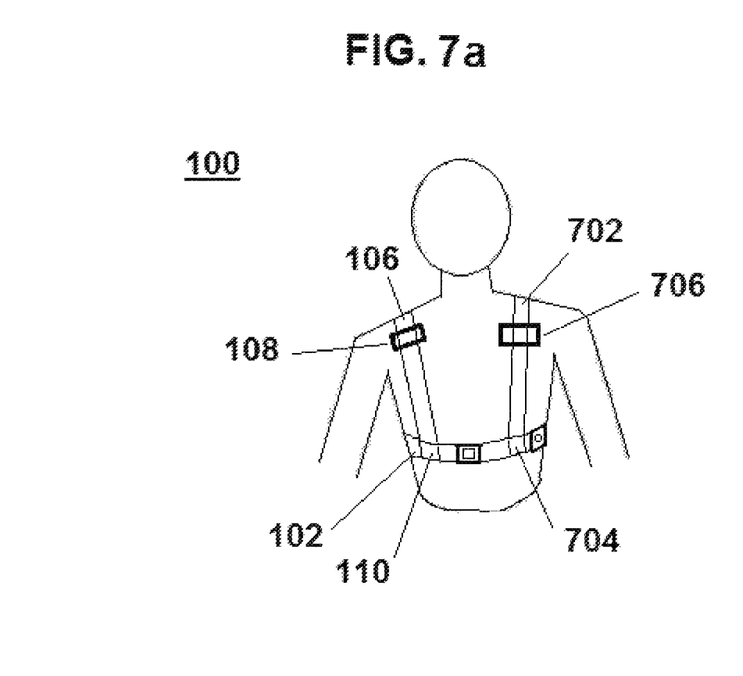
FIG. 7*a*. is a front view of one embodiment of a harness.
Figure 7B:
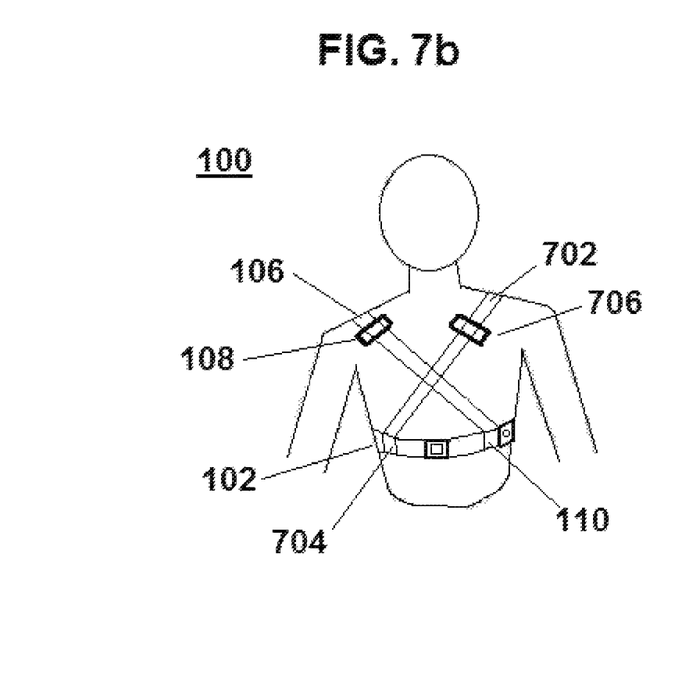
FIG. 7*b*. is a front view of yet another embodiment of a harness.

Referring now to FIGS. 7*a* and 7*b*, the monitor and harness assembly 100 of FIG. 1 further comprises a third retaining means 702, with a first and second end. In one or more embodiments, the first and second ends of the third retaining means 702 may be fixedly or removably attached to the first retaining means 102 the first end towards the front of the user 704 and the second end towards the rear of the user (not pictured).

The third retaining means 702 may further comprise an adjustment means 706. The adjustment means 706 may comprise one or more of a buckle, a snap, a hook and pile closure, a tension adjustment or a means of adjustment of similar physical use or characteristics.

The configuration of the third retaining means may vary with use and the specific embodiments shown here in FIG. 7a and FIG. 7b are of exemplary use, not a limitation on the design.

We claim:

1. A motion artifact reduction apparatus comprising:
a harness,
at least one sleeve body with a first end and a second end,
a means for removably attaching the first end and the second end of the at least one sleeve body to each other,
at least one sensor port disposed on the harness, the at least one sensor port is configured to support a sensor of a plurality of two-part dry electrocardiogram ("ECG") sensors,
the plurality of two-part dry ECG sensors comprising a contact surface with a diameter and a first and second support, the first support comprising a harness body and the second support comprising a spring, wherein the spring is configured to provide a normal force to the contact surface to a user's body; and
a fully reusable and removable annular self-adhesive part, with an inner diameter and an outer diameter, the inner diameter of which is configured to conform to the contact surface diameter of the at least one of a plurality of the two-part dry ECG sensors thereby constraining a shear force of the at least one of the plurality of the two-part dry ECG sensors to the user's body,
wherein the first end and the second end of the sleeve body may be attached to each other thus positioning the sensor port which supports the at least one of a plurality of the two-part dry ECG sensors thus producing two independent and simultaneous forces, normal and shear, towards the user's body at the at least one of a plurality of advantageous locations on the user's body, to reduce motion artifacts arising from increased electrical impedance of the at least one of a plurality of two-part dry ECG sensors,
wherein the harness body comprises an outer layer and an inner layer,
wherein the harness body comprises an outer layer and an inner layer,
wherein the contact surface is disposed on a first side of the outer layer that faces away from the inner layer,
wherein the sensor is further connected to a cable, and
wherein a first end of the cable is connected to the sensor and a second end of the cable is connected to the spring.

2. The motion artifact reduction apparatus of claim 1, wherein the removable annular self-adhesive part further comprises a silicone gel.

3. The motion artifact reduction apparatus of claim 1, wherein the at least one of a plurality of two-part sensors is configured to provide a force normal towards the user's body.

4. The motion artifact reduction apparatus of claim 1, wherein the cable provides an electrical connection between the at least one of the plurality of two-part dry ECG sensors and the spring.

5. The motion artifact reduction apparatus of claim 4, wherein the spring is disposed on a side of the inner layer that faces the outer layer.

6. A kit for use in performing an electrocardiogram ("ECG") with motion artifact reduction, the kit comprising a harness, at least one removable attachable sleeve body with a first end and a second end, at least one sensor port disposed on the harness, at least one of a plurality of two-part dry ECG sensors supported by the sleeve body and comprising a contact surface with a diameter and a first and second support, the first support comprising a harness body and the second support which is disposed a spring spring is configured to provide a normal force to the contact surface to a user's body; and a fully reusable and removable annular self-adhesive part, with an inner dimeter and an outer diameter, the inner diameter which is configured to conform to the contact surface diameter of the at least one of the plurality of two-part dry ECG sensors thereby contrasting a shear force of the at least one of the plurality of two-part dry ECG sensors to the user's body,
wherein the first end and the second end of the sleeve body may be attached to each other thus positioning the sensor port which supports one of a plurality of two-part dry ECG sensors thus producing two independent and simultaneous forces, normal and shear, towards the user's body at least one of a plurality of advantageous locations on the user's body, to reduce motion artifacts arising from increased electrical impedance of the at least one of a plurality of two-part dry ECG sensors,
wherein the harness body comprises an outer layer and an inner layer,
wherein the contact surface is disposed on a first side of the outer layer that faces away from the inner layer,
wherein the contact surface is connected to at least one of the plurality of the two-part dry ECG sensors that is disposed opposite the contact surface on a second side of the outer layer that faces the inner layer,
wherein at least one of the plurality of the two-part dry ECG sensors is further connected to a cable,
and wherein a first end of the cable is connected to at least one of the plurality of the two-part dry ECG sensors and a second end of the cable is connected to the spring.

7. A method of using a motion artifact reduction apparatus comprising the steps of:
providing a harness,
configuring at least one of a plurality of two-part dry electrocardiogram ("ECG") sensors with a contact surface with a contact surface diameter, to provide a normal force to a user's body,
providing at least one sleeve body with first and a second end,
removably attaching the first end and the second end of the at least one sleeve body to each other,
providing the at least one sensor port disposed on the harness, configuring the at least one sensor port to support one of a plurality of two-part dry ECG sensors;
providing the at least one of a plurality of two-part dry ECG sensors comprising the contact surface with the contact surface diameter and a first and second support, the first support comprising a harness body and the second support comprising a spring configuring the spring to provide a normal force to the contact surface to a user's body; and
providing a fully reusable and removable annular self-adhesive part, with an inner diameter and an outer diameter, configuring the inner diameter to conform to the contact surface diameter of the at least one of a plurality of the two-part dry ECG sensors thereby constraining a shear force of the at least one of the plurality of two-part dry ECG sensors to the user's body, attaching the first end and the second end of the sleeve body to each other this positioning the sensor port which supports the at least one of a plurality of the two-part dry ECG sensors thus producing two independent and simultaneous forces, normal and shear, towards the user's body at the at least one of a plurality of advantageous locations on the user's body, to reduce motion artifacts arising from increased electrical impedance of the at least one of a plurality of the two-part dry ECG sensors, wherein the harness body comprises an outer layer and an inner layer, wherein the contact surface is disposed on a first side of the outer layer that faces away from the inner layer, wherein the contact surface is connected to at least one of the plurality of the two-part dry ECG sensors that is disposed opposite the contact surface on a second side of the outer layer that faces the inner layer, wherein at least one of the plurality of the two-part dry ECG sensors is further connected to a cable, and wherein a first end of the cable is connected to at least one of the plurality of the two-part dry ECG sensors and a second end of the cable is connected to the spring.

8. The method of using a motion artifact reduction apparatus of claim 7, wherein the step of providing a fully reusable and removable annular self-adhesive part, with an inner diameter and an outer diameter, configuring the inner diameter to conform to the contact surface diameter of the at least one of a plurality of the two-part dry ECG sensors thereby constraining the shear force of the at least one of the plurality of two-part dry ECG sensors to the user's body further comprises providing a fully reusable and removable annular self-adhesive part comprising a silicone gel.

9. The method of using a motion artifact reduction apparatus of claim 7, wherein the step of providing at least one of a plurality of the two-part dry ECG sensors further comprises the step of proving at one of a plurality of two-part sensors which is configured to provide a force normal towards the user's body by means of a hyper-elastic material compressing the spring backing.

* * * * *

UNITED STATES PATENT AND TRADEMARK OFFICE
CERTIFICATE OF CORRECTION

PATENT NO. : 11,033,235 B2  
APPLICATION NO. : 14/037695  
DATED : June 15, 2021  
INVENTOR(S) : Sonal Tambe, Pramod Deshmukh and Swanand Sardesai Page 1 of 1

It is certified that error appears in the above-identified patent and that said Letters Patent is hereby corrected as shown below:

In the Claims

In Claim 6, Column 6, Line 7, which reads, "a spring spring is" should read --a spring is--

In Claim 6, Column 6, Line 10, the word "dimeter" should be --diameter--

Signed and Sealed this  
Fourteenth Day of September, 2021

Drew Hirshfeld  
*Performing the Functions and Duties of the*  
*Under Secretary of Commerce for Intellectual Property and*  
*Director of the United States Patent and Trademark Office*